(12) United States Patent
Tekely et al.

(10) Patent No.: US 8,283,922 B2
(45) Date of Patent: Oct. 9, 2012

(54) EFFICIENT HETERONUCLEAR DECOUPLING BY QUENCHING ROTARY RESONANCE IN SOLID-STATE NMR

(75) Inventors: Piotr Tekely, Vandoeuvre-les-Nancy (FR); Markus Weingarth, Paris (FR); Geoffrey Bodenhausen, Paris (FR)

(73) Assignees: Brukar BioSpin AG, Faellanden (CH); Ecole Polytechnique Federale de Lausanne (EPFL), Lausanne (CH); Centre National de la Recherche Scientifique (CNRS), Paris (FR)

( * ) Notice: Subject to any disclaimer, the term of this patent is extended or adjusted under 35 U.S.C. 154(b) by 480 days.

(21) Appl. No.: 12/461,634

(22) Filed: Aug. 19, 2009

(65) Prior Publication Data

US 2010/0052673 A1     Mar. 4, 2010

(30) Foreign Application Priority Data

Aug. 25, 2008   (EP) .................................... 08014973

(51) Int. Cl.
*G01V 3/00* (2006.01)
(52) U.S. Cl. ........................................ 324/307; 324/312
(58) Field of Classification Search .................. 324/307, 324/309, 312
See application file for complete search history.

(56) References Cited

U.S. PATENT DOCUMENTS

| | | | | | |
|---|---|---|---|---|---|
| 5,117,186 | A | * | 5/1992 | Burum et al. | 324/307 |
| 5,229,718 | A | * | 7/1993 | Cory | 324/307 |
| 5,260,656 | A | * | 11/1993 | Cory | 324/309 |
| 5,327,085 | A | * | 7/1994 | Cory | 324/307 |
| 6,184,683 | B1 | * | 2/2001 | Emsley et al. | 324/309 |

OTHER PUBLICATIONS

Markus Weingarth, et al. "Low-power decoupling at high spinning frequencies in high static fields", Journal of Magnetic Resonance 199 (2009) 238-241.
Yu Y. et al. "An Efficient Broadband Decoupling Sequence for Liquid Crystals", Journal of Magnetic Resonance, Academic Press, Orlando, FL, US, vol. 130, No. 2, Feb. 1, 1998, pp. 317-320.
Liu S-F. et al. "A Robust Technique for Two-Dimensional Separation of Undistorted Chemical-Shift Anisotropy Powder Patterns in Magic-Angle-Spinning NMR", Journal of Magnetic Resonance, Academic Press, Orlando, FL, US, vol. 155, No. 1, Mar. 1, 2002, pp. 15-28.

(Continued)

Primary Examiner — Louis Arana
(74) Attorney, Agent, or Firm — Paul Vincent (57) ABSTRACT

A method for heteronuclear decoupling in fast magic-angle spinning NMR measurements comprises application of a decoupling RF-pulse sequence with a decoupling-field amplitude $v_1^I$ on spins of a first nucleus and of an excitation pulse on spins of a second nucleus, the sequence comprising m blocks of pulses, with m≥4, each block comprising an N-fold repetition of a pair of pulses with pulse width $\tau_p$ and phases whereby $\tau_p$ is equal for all pulses, whereby the phase of the pulse pair of the (i+1)-th block is inverted with respect to the pulse pair of the i-th block, with i=1 ... m−1 and i is an odd number, whereby the pulses within each pair are phase inverted, whereby a phase shift is carried out after each j-th block, with j is an even number. The efficiency of the inventive method compares favorably with CW, TPPM, SPINAL and XiX decoupling methods at medium and high RF amplitudes, particularly under rotary resonance conditions.

12 Claims, 7 Drawing Sheets

OTHER PUBLICATIONS

Hu B. et al. "Comparison of several hetero-nuclear dipolar recoupling NMR methods to be used in MAS HMQC/HSQC", Journal of Magnetic Resonance; Academic Press, Orlando, FL, US, vol. 192 No. 1, May 1, 2008, pp. 112-122.

Markus Weingarth et al. "Efficient heteronuclear decoupling by quenching rotary resonance in solid-state NMR", Chemical Physics Letters, North-Holland, Amsterdam, vol. 466, Oct. 18, 2008, pp. 247-251.

Tekely P. et al. "Effect of proton spin exchange on the residual. <13>C MAS NMR linewidths. Phase-modulated irradiation for efficient heteronuclear decoupling in rapidly rotating solids", Journal of Magnetic Resonance: Series A, Academic Press, Orlando, FL, US, vol. 107, No. 2, Apr. 1, 1994, pp. 129-133.

Hodgkinson et al. "Heteronuclear decoupling in the NMR of solids", Progress in Nuclear Magnetic Resonance Spectroscopy, Pergamon Press, Oxford, GB, vol. 46, No. 4, Sep. 1, 2005, pp. 197-222.

Kotecha M. et al. "Efficient low-power heteronuclear decoupling in <13>C high-resolution solid-state NMR under fast magic angle spinning", Magnetic Resonance in Chemistry, John Wiley, Chichester, GB, vol. 45, No. S1, Dec. 1, 2007, pp. S221-S230.

Eden M. et al. "Pulse sequence symmetries in the nuclear magnetic resonance of spinning solids: Applicationto heteronuclear decoupling", Journal of Chemical Physics, New York, NY, US, vol. 111, No. 4, Jul. 22, 1999, pp. 1511-1519.

Levitt M.H. "Symmetry in the design of NMR multiple-pulse sequences", Journal of Chemical Physics, New York, NY, US, vol. 128, No. 5, Feb. 7, 2008, pp. 52205-52225.

* cited by examiner

EFFICIENT HETERONUCLEAR DECOUPLING BY QUENCHING ROTARY RESONANCE IN SOLID-STATE NMR

This application claims Paris Convention priority of EP 08 014 973.5 filed Aug. 28, 2008 the entire disclosure of which is hereby incorporated by reference.

BACKGROUND OF THE INVENTION

The invention concerns a method for heteronuclear decoupling in fast magic-angle spinning nuclear magnetic resonance measurements of solid samples.

Efficient heteronuclear decoupling is one of the most challenging requirements that must be fulfilled to obtain high-resolution NMR spectra of solids. In powders containing directly bonded dilute spins $S={}^{13}C$ and abundant spins $I={}^{1}H$, efficient proton decoupling requires a reduction of the heteronuclear dipolar interactions by no less than three orders of magnitude. In polycrystalline or amorphous samples studied by magic-angle spinning (MAS) with slow spinning frequencies $\nu_{rot}$ of a few kHz, continuous-wave (CW) irradiation of the abundant I spins with an RF amplitude (also known as nutation or Rabi frequency $\nu_1^I = -\gamma B_1$) in the range $60 < \nu_1^I < 80$ kHz remains the simplest way to achieve efficient heteronuclear decoupling. At higher spinning speeds, more elaborate schemes have been proposed that use $\pi$ phase shifted (XiX) [1,2] or two-pulse phase-modulated (TPPM) techniques [3]. The success of these methods has lead to renewed interest in the intricate mechanisms underlying efficient decoupling in rotating solids [4]. Several variants of TPPM [5-8] and more sophisticated decoupling schemes have been developed [9-11].

Recent progress in the design of MAS probes and in superconducting magnet technology, fuelled by the apparently unquenchable demand for enhanced sensitivity and spectral resolution, opens the way to very fast spinning frequencies and to ever-increasing static fields. Higher spinning frequencies lead to a more effective averaging of dipolar interactions. It may be useful to recouple dipolar interactions when they give access to structural information. Many recent methodological developments deliberately exploit recoupling to drive the transfer of magnetization from one spin to another. Yet, recoupling can also occur unwittingly, so that the efficiency of heteronuclear decoupling is compromised. Once identified, it is possible to combat these deleterious effects by suitable phase-modulated schemes.

New recoupling schemes require the design of appropriately tailored RF pulse sequences [12]. One of the simplest methods to recouple dipolar interactions in rotating solids is known as rotary resonance recoupling ($R^3$) [13]. It consists in applying an unmodulated continuous-wave (CW) RF field with an amplitude $\nu_1$ adjusted to fulfil one of the conditions $\nu_1 = n\nu_{rot}$ with $n = \frac{1}{2}$, 1 and 2 [13-14]. Besides the recovery of the chemical shift anisotropy (CSA) at $n=1$ and 2, the recoupling of homonuclear interactions can occur at $n=\frac{1}{2}$ and 1, while heteronuclear interactions are recoupled for $n=1, 2, 3, \ldots$. Recoupling by rotary resonance has been exploited both for structural studies and to induce a transfer of magnetization [12-19].

However, rotary resonance can also manifest itself through a partial breakdown of the efficiency of heteronuclear dipolar decoupling [20, 21], leading to a broadening of the resonances of dilute spins S. To avoid this undesirable broadening, the nutation frequency should be at least 4 times higher than the spinning frequency, i.e., $\nu_1^I > 4\nu_{rot}$ [8, 22]. Clearly, with increasing spinning speeds (up to 70 kHz nowadays), it becomes more and more challenging to avoid rotary resonance interferences. Yet, surprisingly, rotary resonance-induced line broadening seems to be perceived so far as inevitable collateral damage of the combination of decoupling and spinning.

[30] discloses a broadband decoupling sequence designed for liquid crystals which is based on a phase modulation of pulses with phase shifts through small angles.

[31] refers to a recoupling method and discloses a magic angle spinning experiment for separating undistorted quasi-static chemical shift powder patterns, using only 360° pulses with suitable phases which makes the spectral patterns insensitive to pulse length errors and other imperfections.

Object of the invention is to present a method that allows one to quench the above described type of interference to a large extent.

SUMMARY OF THE INVENTION

This object is achieved by a method according to the independent claim.

The inventive method for heteronuclear decoupling in fast magic-angle spinning nuclear magnetic resonance measurements, comprises application of a decoupling RF-pulse sequence with a nutation frequency $\nu_1^I$ on spins (I) of a first kind of nucleus and of an excitation pulse on spins (S) of a second kind of nucleus, the decoupling RF-pulse sequence comprising m blocks of pulses, with $m \geq 4$, each block comprising a N-fold repetition of a pair of pulses $(\tau_p)_x(\tau_p)_{-x}$, $(\tau_p)_y(\tau_p)_{-y}$, $(\tau_p)_{-x}(\tau_p)_x$, or $(\tau_p)_{-y}(\tau_p)_y$ with pulse duration $\tau_p$ and phases x, -x, y, -y, whereby $N > 1$ and N is an integer number, whereby $\tau_p$ is equal for all pulses, whereby the pulse phases of all pulse pair of the (i+1)-th block are inverted with respect to the pulse pair of the i-th block, with $i=1 \ldots m-1$ and i is an odd number, whereby the pulses $(\tau_p)_x$, $(\tau_p)_{-x}$, $(\tau_p)_y$, $(\tau_p)_{-y}$ within each pair $(\tau_p)_x(\tau_p)_{-x}$, $(\tau_p)_y(\tau_p)_{-y}$ are phase inverted, whereby a phase shift of the pulses is carried out after each j-th block, with $j < m$ and j is an even number.

Because of the phase inversion of the pulse pairs of neighboring blocks the first pulse of the i-th pair and the second pulse of the (i+1)-th pair have the same phase x or y. The inventive method is not limited to phase shifts between two phases x, y. When choosing $m \geq 6$ further phase shifts are possible.

Preferably the pulse sequence is repeated M times, whereby M is a positive number, in particular until the signal of the spins (S) of the second nucleus has decayed. The number of possible repetitions can vary in a wide range and depends on the line width of the signal of the nucleus to be observed.

In a highly preferred variant N is an odd number. Sequences with an odd number of repetitions of the pulse pairs show a significantly better performance.

For practical use it is preferred to chose $m=4$ and $j=2$.

In an advantageous variant of the inventive method the phase shift after each j-th block is different from 180°. In this case the phase shift after the j-th block is not a simple phase inversion.

In a preferred variant the phase shift after each j-th block is equal to 90°.

It is also possible to carry out the inventive method whereby the phase shift after each j-th block is 0°. This simplified variant can also be used with NMR apparatuses which are not capable of performing phase shifts other than 180°.

Advantageously the pulse duration $\tau_p$ is optimized for the nutation frequency $\nu_1^I$ for maximum peak height of the signals of the spins (S) of the second nucleus. The optimization is carried out during application of the decoupling RF field. The optimized value of the pulse duration $\tau_p$ is used during the whole sequence.

The advantages of the inventive method are highly emphasized if the rotary resonance conditions $v_1^I = nv_{rot}$ are fulfilled, with n is an integer number, since state of the art methods show a poor efficiency under the rotary resonance conditions, whereas the inventive method results in a good performance independent of the existence of rotary resonance conditions.

In order to reduce dissipation of power it is advantageous to choose $v_1^I < 100$ kHz, preferably $v_1^I < 50$ kHz. The inventive method is by far superior to state of the art methods in the range of said decoupling nutation frequencies.

In another advantageous variant of the inventive method decoupling nutation frequencies $v_1^I < v_{rot}$ are used. Such low-amplitude decoupling can be used to alleviate interference effects.

DESCRIPTION OF THE PREFERRED EMBODIMENT

Polycrystalline powders of L-alanine and calcium formate with natural isotopic abundance, and of uniformly $^{13}C$, $^{15}N$-labelled L-alanine and L-glycine, were used without further purification. All experiments were performed on a Bruker spectrometer operating at 9.4 T (Larmor frequency 400.2 MHz for protons), equipped with a 2.5 mm triple resonance MAS probe. In all experiments, cross-polarization (CP) was used to enhance the carbon-13 magnetization, and the spinning frequency was set to $v_{rot}$=30 kHz. The carrier frequency $v_0^I$ of the decoupling RF field applied to the protons I was systematically placed on-resonance for the protons that are directly attached to the $^{13}C$ nuclei under observation.

Starting from the original scheme employing simple π phase shifts [1], a new supercycled scheme aimed at attenuating rotary resonance interferences during heteronuclear decoupling has been developed. The Phase-Inverted Supercycled Sequence for Attenuation of Rotary ResOnance (PISSARRO) is composed of pulse pairs $(\tau_p)_x(\tau_p)_{-x}$, $(\tau_p)_{-x}(\tau_p)_x$, $(\tau_p)_{-y}(\tau_p)_y$ and $(\tau_p)_y(\tau_p)_{-y}$, each of which is repeated N times (typically N=5, see below) to form a block. In the PISSARRO scheme shown in FIG. 1 four blocks are combined, but other numbers of blocks can also be used. After the combination of phase inverted blocks $(\tau_p)_x(\tau_p)_{-x}$, and $(\tau_p)_{-x}(\tau_p)_x$ a phase shift, for example 90°, is carried out, thereby shifting the phase from x to y (phase shifts other than 90° are also possible). By constructing such supercycles [9, 23], rotary resonance interferences can be attenuated and higher order heteronuclear terms can be minimized [9]. The decoupling efficiency of the new scheme has been compared with well-known decoupling methods such as CW, TPPM [3], SPINAL-64 [24] and XiX [1, 2] over a wide range of nutation frequencies $40 < v_1^I < 140$ kHz. For the TPPM sequence, the pulse duration $\tau_p$ and phase angle φ were optimized for each nutation frequency $v_1^I$, $\tau_p$ being varied in the vicinity of the duration of an ideal π pulse, the phase angles φ being varied around ±15°. For a given nutation frequency $v_1^I$, the optimal pulse durations for the SPINAL-64 experiments were found to be close to those for TPPM. For XiX decoupling, the pulse duration $\tau_p$ has been optimized around the recommended condition $\tau_p = 2.85 \cdot \tau_{rot}$ [2]. For the PISSARRO sequence, the pulse duration $\tau_p$ was optimized for each nutation frequency $v_1^I$ in the interval $0.1 \cdot \tau_{rot} < \tau_p < 1.1 \cdot \tau_{rot}$.

To simulate the $^{13}C$ spectrum of calcium formate with XiX and PISSARRO decoupling at the n=2 rotary resonance condition, isolated $^{13}C$-$^1H$ spin pairs with an internuclear distance of 1.09 Å have been assumed, neglecting chemical shift anisotropies. All simulations used the SIMPSON program [25]. Powder averaging was achieved with 17 γ-angles and 615 α, β-orientations using the Zaremba-Conroy-Wolfsberg (ZCW) scheme [25].

Figure 2:
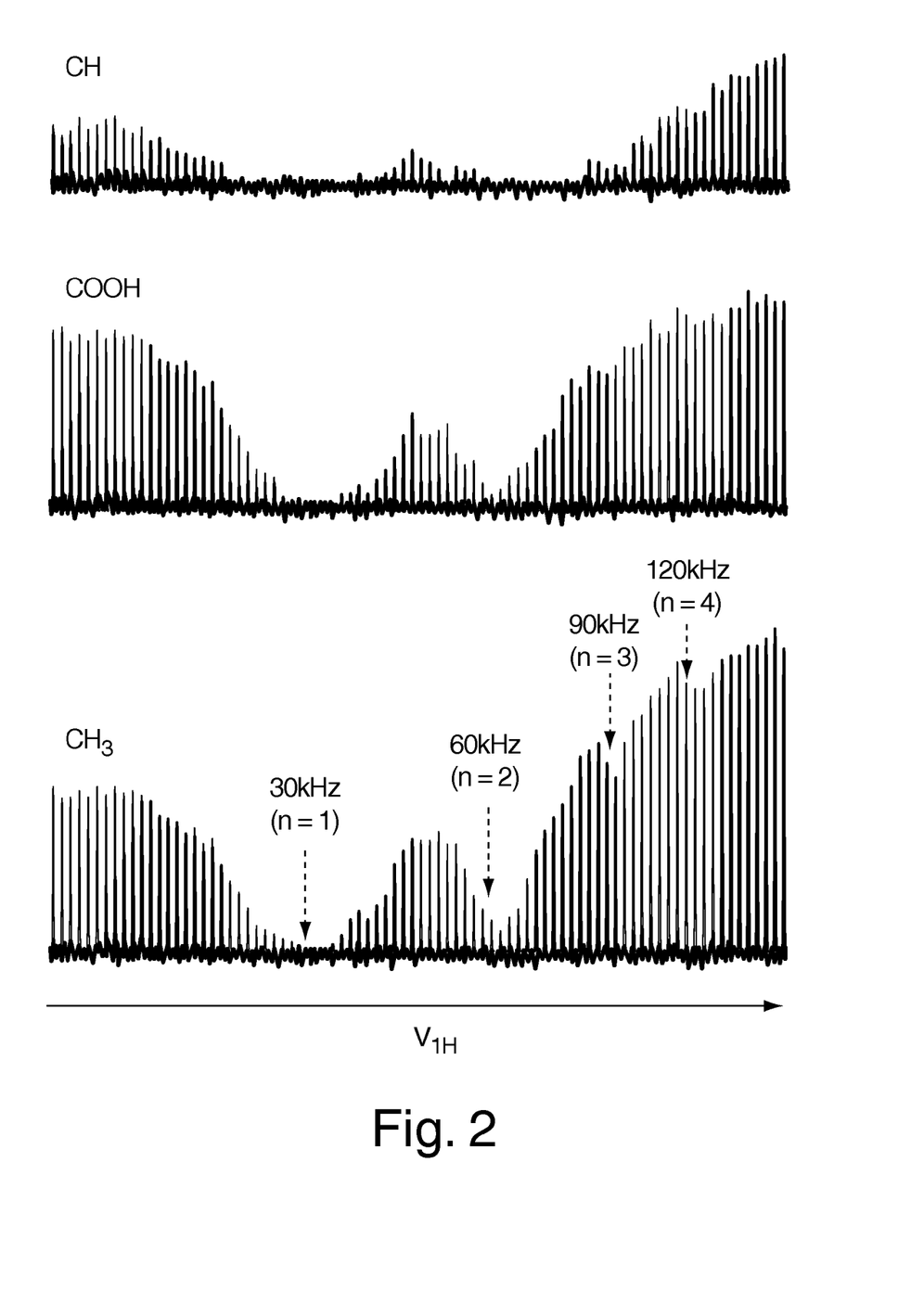
FIG. 2 shows the efficiency of CW-decoupling in the presence of magic angle spinning (MAS) with a spinning frequency $v_{rot}$=30 kHz. The plots show the $^{13}C$ resonance signals of the $CH_3$, COOH and CH groups in natural abundance L-alanine $NH_3^+CHCH_3COOH$ as a function of the nutation frequency $v_1^I$. Note the broad 'dips' centered at $v_1^I$=30, 60, 90 and 120 kHz, i.e., near the rotary resonance conditions $v_1^I = n \, v_{rot}$ with n=1, 2, 3 and 4.

To illustrate how rotary resonance recoupling can interfere destructively with decoupling in rapidly spinning powders, FIG. 2 shows plots of $^{13}C$ signals of L-alanine in natural abundance recorded with CW decoupling as a function of the nutation frequency $v_1^I$. Besides a dramatic collapse of all peaks in the vicinity of the rotary resonance conditions $v_1^I = n v_{rot}$ with n=1 and 2, the plots reveal that the 'dips' around these recoupling conditions extend symmetrically over a wide range of nutation frequencies $v_1^I$. Although their breadth can be in part ascribed to the inhomogeneity of the RF-field, since rotary resonance is very sensitive to this parameter [15(a)], the fact that the dips are the broadest for the CH group must be due to the strength of the heteronuclear dipolar interactions. Note that for the methyl $CH_3$ and carboxyl COOH groups, the two dips for n=1 and 2 are much broader than would be expected from the magnitudes of the corresponding heteronuclear couplings. This strongly suggests that homonuclear proton-proton dipolar interactions must also contribute to the breadth of these dips [21] by playing an indirect role in the recoupling conditions at n=1 and 2.

Figure 3:
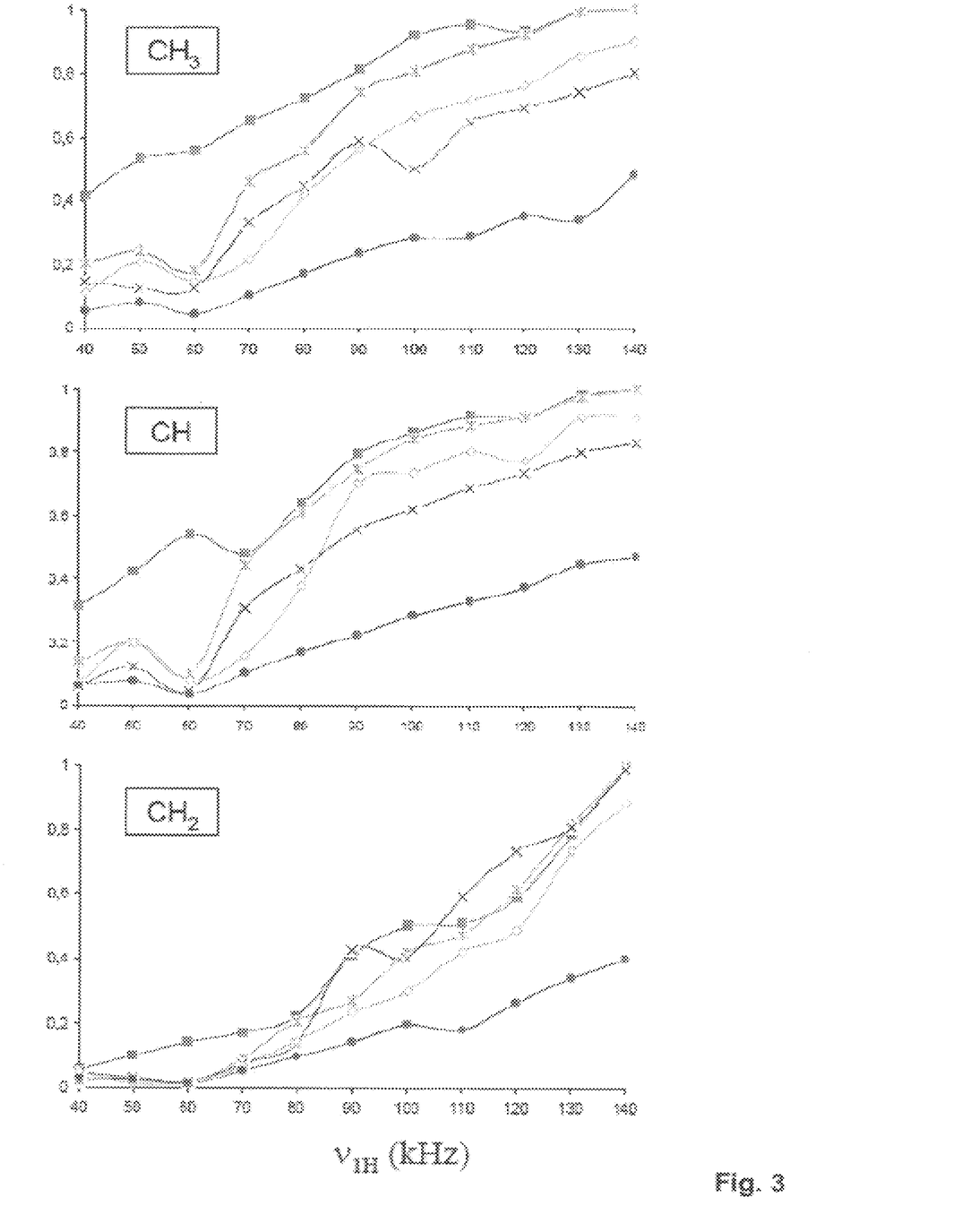
FIG. 3 shows a comparison of the $^{13}C$ peak heights of the $CH_3$, CH and $CH_2$ signals in uniformly $^{13}C,^{15}N$-labelled L-alanine and L-glycine, which give a measure of the decoupling efficiency of various decoupling schemes at $v_{rot}$=30 kHz: PISSARRO (squares), XiX (stars), TPPM (crosses), SPINAL-64 (diamonds) and CW (dots).

Quenching of Interference of Rotary Resonance Recoupling ($R^3$) with Heteronuclear Decoupling The efficiency of different decoupling sequences for the $CH_3$, $CH_2$ and CH groups of uniformly labelled alanine and glycine is shown in FIG. 3 over a wide range of nutation frequencies $v_1^I$ that include rotary resonance conditions $v_1^I = nv_{rot}$ with n=2, 3 and 4. For each resonance, the signal intensities were normalized to S=1 for the PISSARRO scheme using the highest nutation frequency $v_1^I$. Besides the obvious improvement in performance of all phase-modulated schemes compared to CW decoupling, the PISSARRO sequence proved to be the most effective in quenching rotary resonance effects in the range $40 < v_1^I < 100$ kHz. For $CH_3$ and CH groups, it turned out to be the most efficient method over the whole range $40 < v_1^I < 140$ kHz that has been explored. Indeed, for both $CH_3$ and carboxyl groups (the latter not shown), the new scheme using $v_1^I = 90$ kHz is more efficient than TPPM with $v_1^I = 140$ kHz, and for $CH_3$ and CH groups the new method, again using $v_1^I = 90$ kHz, reaches ~80% of the performance of XiX with $v_1^I = 140$ kHz. For the $CH_2$ group of glycine, the PISSARRO scheme was only inferior to the TPPM sequence in the range of $110 < v_1^I < 130$ kHz, while for $v_1^I = 140$ kHz the new method showed the same performance as XiX and TPPM. Obviously, a high decoupling efficiency with moderate nutation frequencies $v_1^I < 100$ kHz is particularly attractive for heat-sensitive samples, such as proteins with high water and salt content, where high RF power levels can be harmful.

Figure 4:
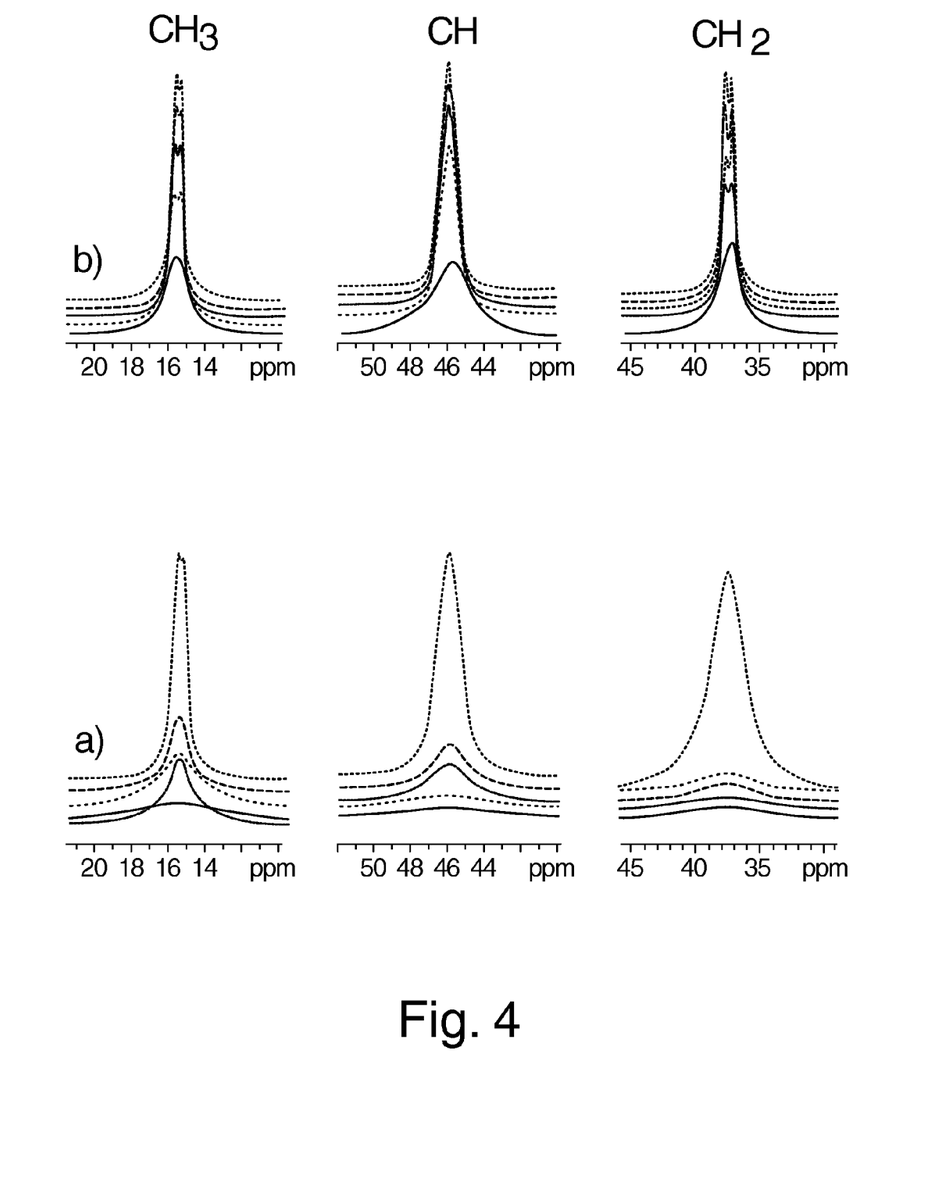
FIG. 4 shows a comparison of the $^{13}C$ peak heights of the $CH_3$, CH and $CH_2$ signals in uniformly $^{13}C,^{15}N$-labelled L-alanine and L-glycine, acquired at $v_{rot}$=30 kHz and (a) $v_1^I$=60 and (b) $v_1^I$=100 kHz, using PISSARRO (closely spaced, dashed line; upper curve in the FIG. 4b, $CH_3$ plot), XiX (broadly dashed line; second from the top curve in the FIG. 4b, $CH_3$ plot), TPPM (broadly spaced dashed line; fourth from the top curve in the FIG. 4b, $CH_3$ plot), SPINAL-64 (closely spaced, dotted line; third from the top curve in the FIG. 4b, $CH_3$ plot) and CW (solid line; lowermost curve in the FIG. 4b, $CH_3$ plot). The various curves shown in the figures have been displaced relative to each other in the vertical direction to permit illustration of the individual curve shapes.

FIG. 4a allows one to appreciate how sensitive various decoupling schemes are to rotary resonance interference at the n=2 condition ($v_1^I = 60$ kHz and $v_{rot} = 30$ kHz). The relative intensities of the $CH_3$ signals using PISSARRO, XiX, SPINAL-64, TPPM and CW decoupling are 100, 33, 27, 18 and 8% respectively. The $CH_3$ linewidths are 83, 126, 163, 250 and 730 Hz for the five methods that have been compared. Note that areas of the signals are not conserved, since the signal amplitudes are partly transferred to modulation sidebands, as discussed below. For the CH resonance, the relative intensities in FIG. 4a are 100, 18, 14, 8 and 7%, and the corresponding linewidths are 135, 218, 285, 760 and 1250 Hz. For the $CH_2$ resonance, the relative intensities are 100, 12, 12, 13 and 9%, and the corresponding linewidths 250, 440, 1100, 710 and 1230 Hz. Although at the n=2 rotary resonance condition, the amplitude of the $CH_2$ signal observed with PISSARRO remains humble compared to high amplitude decoupling (the efficiency of decoupling at $v_1^I = 100$ kHz is shown in FIG. 4b), the $CH_2$ intensity could be increased by a factor of at least 8 compared to other decoupling schemes at n=2. It should be pointed out that for XiX decoupling, an improved efficiency was observed at n=2 with $\tau_p = 0.85 \cdot \tau_{rot}$, much shorter that the recommended duration $\tau_p = 2.85 \cdot \tau_{rot}$. However, the intensities recorded under such unusual conditions are significantly below those observed with the new decoupling scheme.

Quenching of Modulation Sidebands

Figure 5:
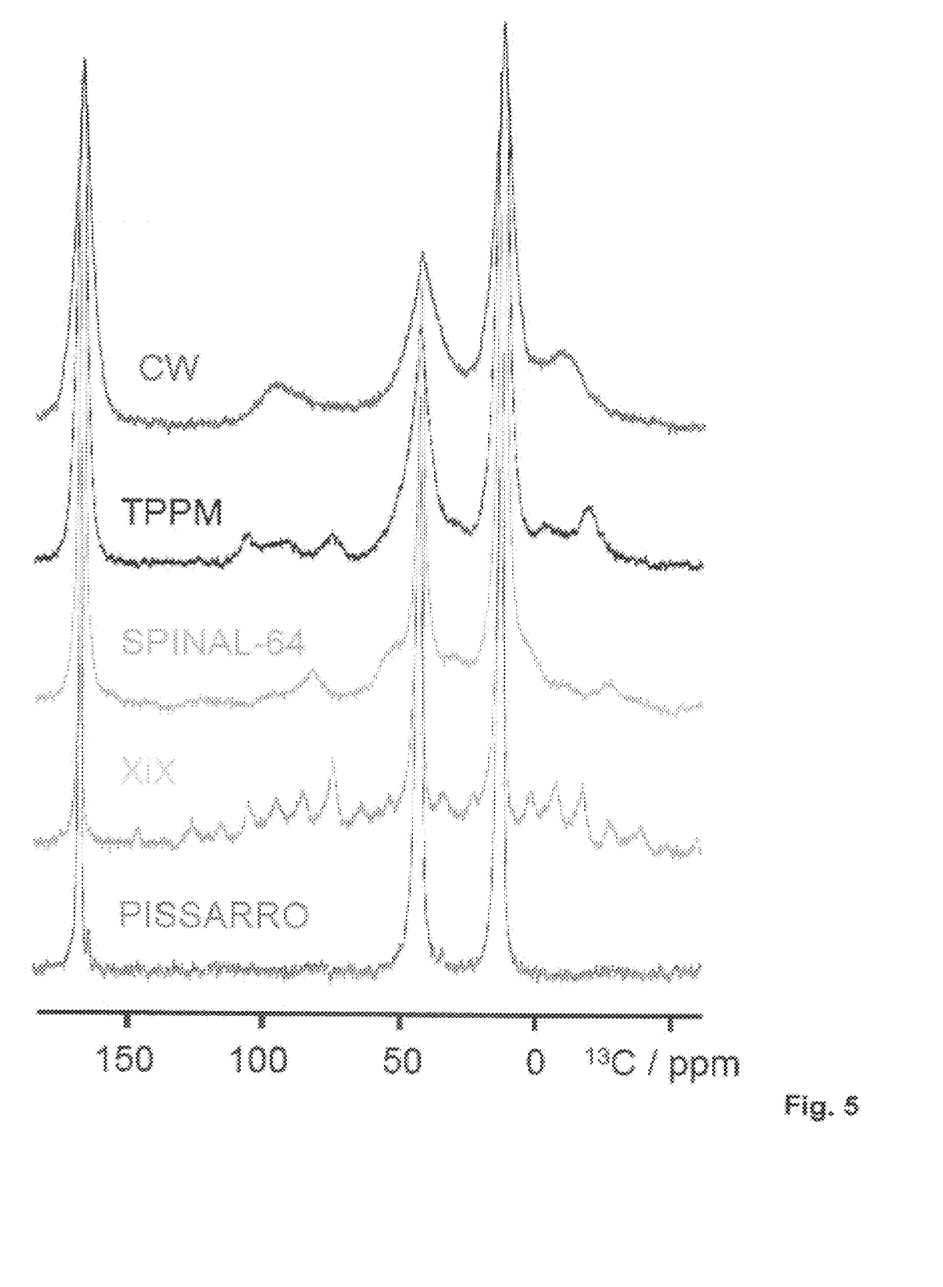
FIG. 5 shows a comparison of experimental spectra of L-alanine recorded with $v_1^I$=60 kHz and $v_{rot}$=30 kHz (n=2), using the CW, TPPM, SPINAL-64, XiX and PISSARRO decoupling schemes. Note the modulation sidebands that are due to the interference of decoupling and spinning. The sidebands completely disappear with the PISSARRO scheme.

Another remarkable advantage of the new PISSARRO scheme is its unique capacity to suppress spurious modulation sidebands, which arise from the interference between the decoupling field and the modulation of dipolar couplings by MAS [3]. FIG. 5 shows spectra recorded at the n=2 rotary resonance condition, with different decoupling schemes optimized for signal intensity. The modulation sidebands show up dramatically for all known techniques except for the new scheme, which offers a remarkably clean spectrum.

Figure 6:
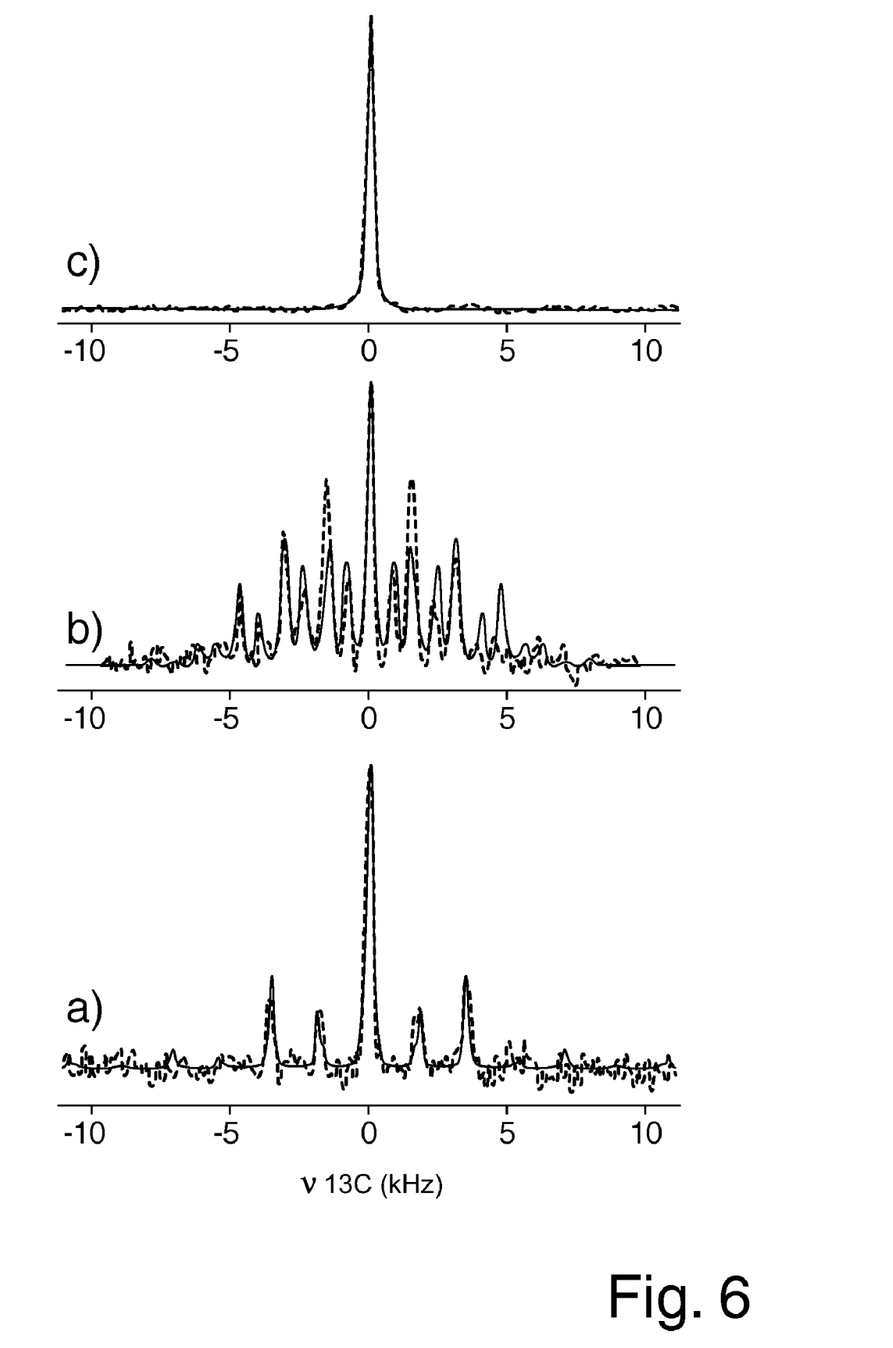
FIG. 6 shows an experimental (dotted line) and simulated (solid line) spectra of calcium formate obtained with $v_1^I$=60 kHz using the (a, b) XiX and (c) PISSARRO schemes. The simulations were calculated for $v_{rot}$=30 kHz with pulse durations (a) $\tau_p$=31.5 us, (b) 32.5 us, and (c) 6.5 us.
Figure 7:
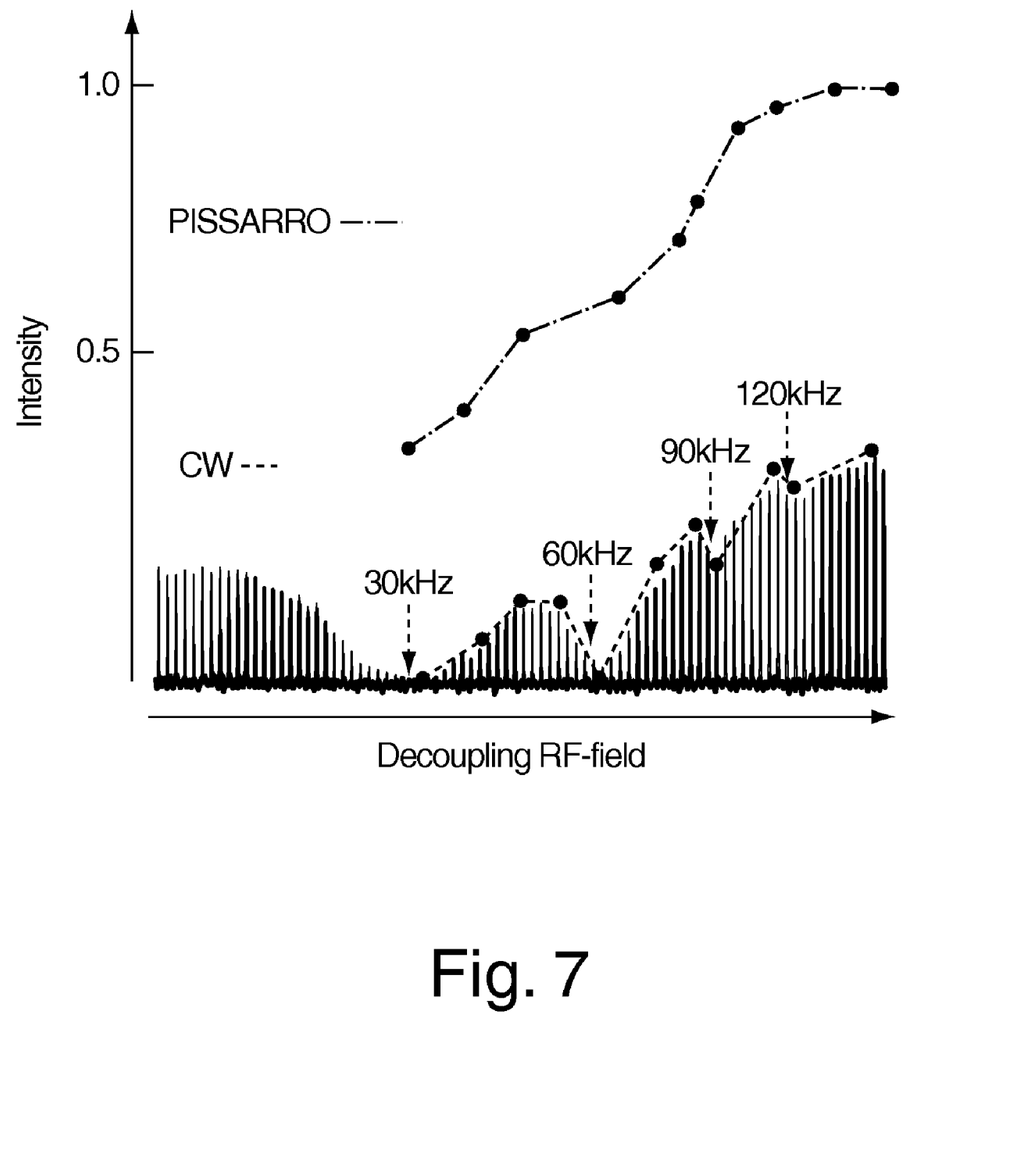
FIG. 7 shows a graphical abstract of the inventive method.

Because of the complexity of the evolution of the magnetization under phase-modulated irradiation and MAS close to the rotary resonance conditions, the combined effects of homo- and heteronuclear dipolar interactions are difficult to handle analytically. To gain a better insight into some basic features of XiX and PISSARRO decoupling, the behaviour of calcium formate $Ca(CHCOO)_2$ with natural $^{13}C$ abundance, which contains reasonably isolated $^{13}C$-$^1H$ spin pairs, has been studied by experiments and simulations. Very similar effects could be observed for the (less well isolated) CH group in uniformly $^{13}C$ enriched L-alanine. As shown in FIG. 6, both the experimental and simulated spectra clearly show the dependence of the modulation sidebands that appear at $v_{ms} = N(\pm v_{rot} \mp 1/\tau_p)$ on the pulse duration $\tau_p$ of XiX decoupling. Thus for $v_{rot} = 30$ kHz and $\tau_p = 31.5$ μs, i.e., $1/\tau_p = 31.746$ kHz, one obtains sidebands at multiples of 1.746 kHz. These modulation sidebands cannot be avoided when optimizing the $\tau_p$ values for the best efficiency of XiX decoupling. On the other hand, experimental and simulated spectra obtained with the PISSARRO scheme with optimized $\tau_p$ values are remarkably free of any spurious sideband signals. Further simulations (not shown) reveal that the magnitudes of the dipolar and CSA interactions, the proton offset as well as the decoupling frequency affect the intensity of the modulation sidebands under XiX decoupling. Extensive numerical simulations will be necessary to probe the influence of homonuclear proton-proton couplings when quenching rotary resonance effects. Indeed, the relevance of such interactions for heteronuclear decoupling in fast spinning solids has been recognized early on [1], and studied experimentally and theoretically under different conditions [1, 9, 26-28]. It is worth noting that the modulation sidebands overlap with their parent signals when $\tau_p$ corresponds to a full rotor period ($v_{rot} = 1/\tau_p$), thus fulfilling one of the recoupling conditions for phase-modulated decoupling [1, 2].

Figure 1:
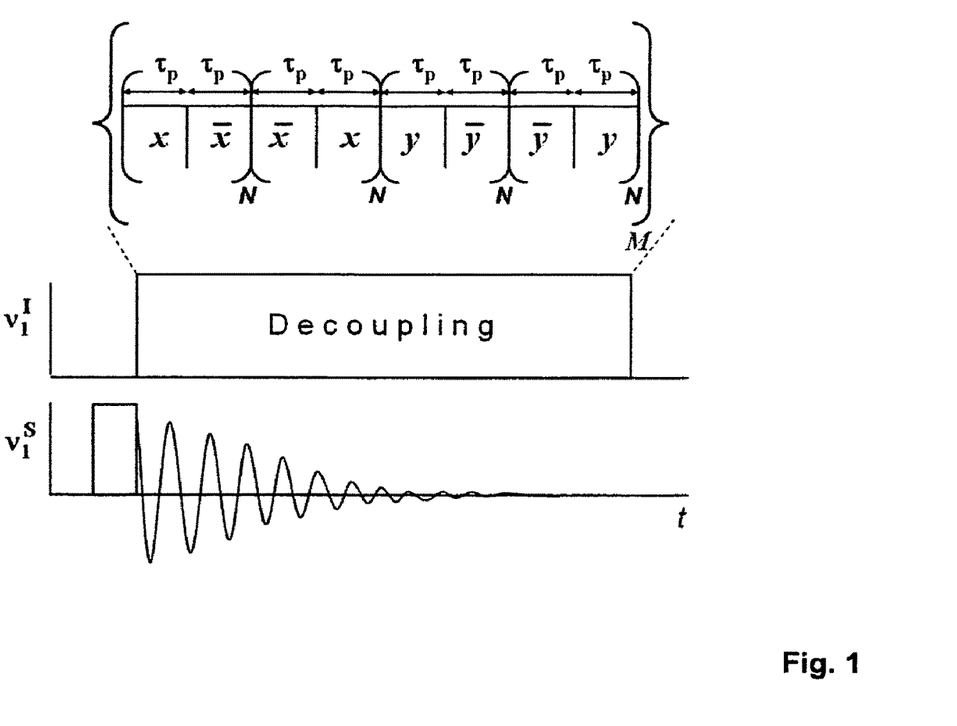
FIG. 1 shows the PISSARRO scheme for efficient heteronuclear decoupling with m=4. The direct excitation of the magnetization of spins S such as $^{13}C$ can be replaced by cross-polarization from abundant spins I such as protons to the S spins.

Finally, it should be noted that a simplified, truncated version of the PISSARRO scheme, using only the first half of the decoupling sequence in FIG. 1, without any 90° phase shifts, also exhibits a significantly improved decoupling efficiency at n=2 compared with other pulse sequences. For $70 < v_1^I < 80$ kHz, it is actually superior to the complete untruncated PISSARRO scheme.

The supercycled PISSARRO sequences with odd numbers of pulse pairs N=3, 5, 7 . . . (usually, N=5) perform significantly better than those with even numbers N=2, 4, . . . . This appears to open further opportunities to improve the quenching of rotary resonance interferences.

Destructive interference due to rotary resonance recoupling also occurs when very fast spinning frequencies $v_{rot} > 30$ kHz are combined with commonly used RF-decoupling schemes. For CH and $CH_2$ resonances observed with spinning frequencies $v_{rot} = 40$ kHz, rotary resonance interferences can extend beyond $v_1^I = 200$ kHz [8] while at $v_{rot} = 70$ kHz such effects occur at $v_1^I = 350$ kHz [22]. All previously known decoupling methods therefore entail the use of ever-increasing RF-amplitudes with increasing nutation frequencies. Of course, low-amplitude decoupling with $v_1^I \ll v_{rot}$ can be used to avoid interference effects. Except for $CH_2$ resonances, this simple approach can compete in efficiency with high amplitude decoupling, provided $v_{rot} > 40$ kHz [8, 29].

A novel heteronuclear decoupling scheme for fast MAS that offers improved decoupling efficiency over a wide range of nutation frequencies $v_1^I$ has been introduced. The-PIS- SARRO decoupling sequence using a single adjustable $\tau_p$ parameter proved to be more effective that the XiX, TPPM, SPINAL-64 and CW methods in quenching rotary resonance interference effects. The new method yields improved resolution and sensitivity for all solid-state NMR spectra recorded with fast spinning with nutation frequencies $\nu_1^I$ close to the n=2 rotary resonance condition. Numerical simulations of PISSARRO decoupling using an experimentally optimized pulse duration $\tau_p$ corroborate the experimental observation that spurious signals due to modulation sidebands are efficiently eliminated. For $CH_3$, COOH and CH groups, PISSARRO decoupling proved to be the most efficient method over the whole range $40<\nu_1^I<140$ kHz that was examined. For the most challenging $CH_2$ groups, PISSARRO decoupling was less efficient than TPPM only in a limited range $110<\nu_1^I<130$ kHz. At $\nu_1^I=140$ kHz the new scheme has the same performance as XiX and TPPM. Since PISARRO decoupling leads to quenching of rotary resonance interferences, one can expect an improved efficiency of low-amplitude decoupling at spinning frequencies $\nu_{rot}>40$ kHz. The inventive method has been exemplary explained for the resonance measurements with dilute spins S=$^{13}$C and abundant spins I=$^1$H. However, the application of the inventive method is not restricted to these nuclei, but can be carried out in analogous manner using spins of other nuclei.

The proposed a new scheme for heteronuclear decoupling designed for fast magic-angle spinning (MAS) is dubbed Phase-Inverted Supercycled Sequence for Attenuation of Rotary ResOnance (PISSARRO). Its efficiency compares favourably with CW, TPPM, SPINAL and XiX decoupling methods at medium and high nutation frequencies, particularly under conditions where the efficiency of decoupling can be affected by undesired rotary resonance effects.

REFERENCES

[1] P. Tekely, P. Palmas, D. Canet, J. Magn. Reson. A 107 (1994) 129-133.
[2] A. Detken, E. H. Hardy, M. Ernst, B. H. Meier, Chem. Phys. Lett. 356 (2002) 298-304.
[3] A. E. Bennett, C. M. Rienstra, M. Auger, K. V. Lakshli, R. G. Griffin, J. Chem. Phys. 103 (1995) 6951-6958.
[4] P. Hodgkinson, Prog. NMR Spectrosc. 46 (2005) 197-222 and references therein.
[5] Z. Gan, R. R. Ernst, Solid State NMR 8 (1997) 153-159.
[6] K. Takegoshi, J. Mizokami, T. Terao, Chem. Phys. Lett. 341 (2001) 540-544
[7] R. S. Thakur, N. D. Kurur, P. K. Madhu, Chem. Phys. Lett. 426 (2006) 459-463.
[8] M. Kotecha, N. P. Wickramasingbe, Y. Ishii, Magn. Reson. Chem. 45 (2007) S221-S230.
[9] M. Eden, M. H. Levitt, J. Chem. Phys. 111 (1999) 1511-1519.
[10] G. DePaëpe, P. Hodgkinson, L. Emsley, Chem. Phys. Lett. 376 (2003) 259-267.
[11] G. Gerbaud, F. Ziarelli, S. Caldarelli, Chem. Phys. Lett. 377 (2003) 1-5.
[12] S. Dusold, A. Sebald, Ann. Rep. NMR Spectrosc. 41 (2000) 185-264.
[13] T. G. Oas, R. G. Griffin, M. H. Levitt, J. Chem. Phys, 89 (1988) 692-695.
[14] N. C. Nielsen, H. Bildsoe, H. J. Jakobsen, M. H. Levitt, J. Chem. Phys. 101 (1994) 1805-1812.
[15] (a) Z. Gan, D. M. Grant, R. R. Ernst, Chem. Phys Lett. 254 (1996) 349-357; (b) Z. Gan, J. Magn. Reson. 183 (2006) 247-253.
[16] (a) K. Takegoshi, S. Nakamura, T. Terao, Chem. Phys. Lett. 344 (2001) 631-637. (b) K. Takegoshi, S. Nakamura, T. Terao, J. Chem. Phys. 118 (2003) 2325-2341.
[17] Z. Gan, J. P. Amoureux, J. Trébosc, Chem. Phys. Lett. 435 (2007) 163-169.
[18] L. Odgaard, M. Bak, H. J. Jakobsen, N. C. Nielsen; J. Magn. Reson. 148 (2001) 298-308.
[19] (a) L. Duma, D. Abergel, P. Tekely, G. Bodenhausen, Chem. Comm. 20 (2008) 2361-2363; (b) L. Duma, D. Abergel, F. Ferrage, P. Pelupessy, P. Tekely, G. Bodenhausen, Chem Phys Chem. 9 (2008) 1104-1108.
[20] T. Nakai, C. A. McDowell, Chem. Phys. Lett. 227 (1994) 639-644.
[21] S. J. Kitchin, K. D. M. Harris, A. E. Aliev, D. C. Apperley, Chem. Phys. Lett. 323 (2000) 490-497.
[22] M. Ernst, A. Samoson, B. H. Meier, J. Chem. Phys. 123 (2005) 064102-1-10.
[23] M. H. Levitt, J. Chem. Phys. 128 (2008) 052205-1-25.
[24] B. M. Fung, A. K. Khitrin, K. Ermolaev, J. Magn. Reson. 142 (2000) 97-101.
[25] M. Bak, J. T. Rasmussen, N. C. Nielsen, J. Magn. Reson. 147 (2000) 296.
[26] M. Ernst, H. Zimmermann, B. H. Meier, Chem. Phys. Lett. 317 (2000) 581-588.
[27] G. DePaëpe, B. Elena, L. Emsley, J. Chem. Phys. 121 (2004) 3165-3180.
[28] M. Leskes, R. S. Thakur, P. K. Madhu, N. D. Kurur, S. Vega, J. Chem. Phys. 127 (2007) 024501-17.
[29] M. Ernst, A. Samoson, B. H. Meier, Chem. Phys. Lett. 348 (2001) 293-302.
[30] Y. Yu, B. M. Fung, J. Magn. Reson. 130 (1998) 317-320.
[31] S-F. Fiu, J-D. Mao, K. Schmidt-Rohr, J. Magn. Reson. 155 (2002) 15-28

We claim:

1. A method for heteronuclear decoupling in magic-angle spinning nuclear magnetic resonance measurements of solid samples, the method comprising the steps of:
   a) applying a decoupling RF-pulse sequence with a nutation frequency $\nu_1^I$ on spins (I) of a first kind of nucleus; and
   b) applying an excitation pulse on spins (S) of a second kind of nucleus, which is different from the first kind of nucleus, wherein the decoupling RF-pulse sequence comprises m blocks of pulses, with m≧4, each block comprising an N-fold repetition of a pair of pulses $(\tau_p)_x(\tau_p)_{-x}$, $(\tau_p)_y(\tau_p)_{-y}$, $(\tau_p)_{-x}(\tau_p)_x$ or $(\tau_p)_{-y}(\tau_p)_y$, wherein $\tau_p$, given in parentheses, is a pulse duration $(\tau_p)$ and x, -x, y, -y, given in subscripts, are pulse phases, wherein N>1 and N is an integer number, $\tau_p$ being equal for all pulses, wherein the pulse phases of all pulses in the pulse pair of the (i+1)-th block are inverted with respect to the pulse pair of the i-th block, with i=1 ... m−1 and i is an odd number, the pulses $(\tau_p)_x$, $(\tau_p)_{-x}$, $(\tau_p)_y$, $(\tau_p)_{-y}$ within each pair $(\tau_p)_x(\tau_p)_{-x}$, $(\tau_p)_y(\tau_p)_{-y}$ being phase inverted, and a phase shift of the pulses $(\tau_p)_x$, $(\tau_p)_{-x}$, $(\tau_p)_y$, $(\tau_p)_{-y}$ is carried out after each j-th block, with j≦m, wherein j is an even number.

2. The method of claim 1, wherein the decoupling RF-pulse sequence is repeated M times, where M is a positive integer number.

3. The method of claim 1, wherein N is an odd number.

4. The method of claim 1, wherein m=4 and j=2.

5. The method of claim 1, wherein the phase shift of the pulses $(\tau_p)_x$, $(\tau_p)_{-x}$, $(\tau_p)_y$, $(\tau_p)_{-y}$ after each j-th block is different from 180°.

6. The method of claim 5, wherein the phase shift of the pulses $(\tau_p)_x$, $(\tau_p)_{-x}$, $(\tau_p)_y$, $(\tau_p)_{-y}$ after each j-th block is equal to 90°.

7. The method of claim 5, wherein the phase shift of the pulses $(\tau_p)_x$, $(\tau_p)_{-x}$, $(\tau_p)_y$, $(\tau_p)_{-y}$ after each j-th block is 0°.

8. The method of claim 1, wherein the pulse duration $\tau_p$ is optimized for the nutation frequency $\nu_1^I$ for maximum peak height of signals of the spins (S) of the second kind of nucleus.

9. The method of claim 1, wherein rotary resonance conditions $\nu_1^I = n\nu_{rot}$ are fulfilled, where n is an integer number and $\nu_{rot}$ is the spinning frequency.

10. The method of claim 1, wherein $\nu_1^I < \nu_{rot}$.

11. The method of claim 1, wherein $\nu_1^I < 100$ kHz.

12. The method of claim 11, wherein $\nu_1^I < 50$ kHz.

* * * * *

UNITED STATES PATENT AND TRADEMARK OFFICE
CERTIFICATE OF CORRECTION

PATENT NO. : 8,283,922 B2  
APPLICATION NO. : 12/461634  
DATED : October 9, 2012  
INVENTOR(S) : Piotr Tekely et al.

It is certified that error appears in the above-identified patent and that said Letters Patent is hereby corrected as shown below:

Please amend the Title Page of the patent to correct Item 73, the first Assignee of record as follows -- ~~Brukar~~Bruker BioSpin AG, Faellanden (CH) --.

Please amend the Title Page to include the omitted fourth Assignee of Record as follows -- Ecole Normale Superieure (ENS), Paris (FR) --.

Signed and Sealed this  
Twelfth Day of February, 2013

Teresa Stanek Rea  
*Acting Director of the United States Patent and Trademark Office*